United States Patent [19]

Faulkner

[11] 4,209,256
[45] Jun. 24, 1980

[54] LIQUID FLOW VIEWING CELL AND METHOD FOR ANALYZING LIQUID STREAM

[75] Inventor: Albert A. Faulkner, Conshohocken, Pa.

[73] Assignee: SmithKline Corporation, Philadelphia, Pa.

[21] Appl. No.: 926,750

[22] Filed: Jul. 21, 1978

[51] Int. Cl.² .............................................. G01N 1/10
[52] U.S. Cl. ..................................... 356/246; 356/39; 356/73
[58] Field of Search ...................... 356/246, 39, 73, 71, 356/72; 250/461; 350/8, 17, 36, 41, 39, 73, 35, 9; 336/410

[56] References Cited

U.S. PATENT DOCUMENTS

| | | | |
|---|---|---|---|
| 3,770,349 | 11/1973 | Sanchez | 356/73 |
| 3,827,555 | 8/1974 | Kamentsky et al. | 356/39 |
| 3,827,804 | 8/1974 | Miller et al. | 356/39 |
| 3,871,770 | 3/1975 | von Behrens et al. | 356/39 |
| 3,916,205 | 10/1975 | Kleinersman | 356/39 |
| 3,924,947 | 12/1975 | Hogg | 356/39 |
| 3,989,381 | 11/1976 | Fulwyler | 356/39 |

OTHER PUBLICATIONS

Pulse Cytophotomer 1CP11, Phywe Aktiengesellschaft 34 Gottingen-Germany.

*Primary Examiner*—John K. Corbin
*Assistant Examiner*—B. W. de los Reyes
*Attorney, Agent, or Firm*—Harding, Earley & Follmer

[57] ABSTRACT

The invention is for a method for analyzing a stream of liquid such as blood and apparatus for carrying out the method. While it is known to present a moving column of liquid in a viewing cell, control of the circumference of the column to control its field size and lighting the column from the end opposite the viewing end has not been accomplished. The invention involves the method of passing a first liquid in a column in a confined space to a transparent panel, introducing one or more liquids of different colors to form a hollow column exterior of the first column, exhausting the liquids from adjacent the panel, directing light upwardly at the lower ends and through the columns and varying the pressure of one or more of the liquids to vary the circumference and speed of the first column. Apparatus is provided to carry out the method.

6 Claims, 7 Drawing Figures

LIQUID FLOW VIEWING CELL AND METHOD FOR ANALYZING LIQUID STREAM

TECHNICAL FIELD

This invention is in the field of analyzing particles in streams of liquid.

BACKGROUND OF PRIOR ART

It is known in the prior art to present an upwardly flowing column of liquid in a cell which has a transparent cover over the column permitting the viewing of the column. Light has been directed downwardly into the column to facilitate viewing. Viewing with a microscope by an observer and viewing with devices for counting particles, measuring particle sizes and measuring dye content in particles is well known. Reference may be had to *Pulse Cytophotometer* 1CP 11 by Phywe Ag, D-3400, Gottingen, West Germany. The heretofore known cells have presented a column of liquid which has a fixed diameter without any way to adjust the optimum diameter of the column for the instrument used in viewing the column in the cell. Further, lighting the column of liquid from the viewing end of the cell provides inadequate lighting.

BRIEF SUMMARY OF THE INVENTION

A liquid flow viewing cell has a body having a main passageway with opposed ends terminating within the body. A first supply passageway is connected adjacent to one end of the main passageway and an exhaust passageway is connected adjacent to the other end of the main passageway. At least a second supply passageway is connected to the main passageway at a point between the connections of the supply and exhaust passageways to the main passageway. The body is transparent opposite the ends of the main passageways. A light adjacent one end of the main passageway is directed towards the other viewing end of the passageway. A system supplies liquids to each of the supply passageways at predetermined pressures to move the liquids through the main passageway and the exhaust passageway.

In the method of the invention for presenting a stream of liquid for viewing, a first liquid to be viewed is passed upwardly in a first column in a confined space to a transparent panel through which the column can be viewed. A second liquid of a color differing from the color of the fist liquid is introduced into the confined space to form a second upwardly moving column exterior of the first column. A discharge system carries off the first and second liquids from underneath the viewing panel. Light is directed upwardly at the lower end of the columns of liquid towards the transparent panel. The pressure of one or more of the liquids is varied to vary the diameter of the first column of liquid. If desired, a third liquid may be introduced into the confined space at a point opposite the point of introduction of the second liquid. The color of the third liquid may be the same as the color of the second liquid or may differ in color from both the first and second liquids.

The apparatus and method of the invention overcome the problem of the prior art of having a column of liquid which cannot be accommodated to the field of a viewing device since by varying the relative pressures of the liquid to be viewed and an additional liquid surrounding the liquid to be viewed, the diameter of the liquid to be viewed can be varied. Further, the apparatus and method of the invention provide for the introduction of light at the end of the column opposite to the viewing end which provides far superior illumination to that provided by the prior art.

DETAILED DESCRIPTION

Figure 1:
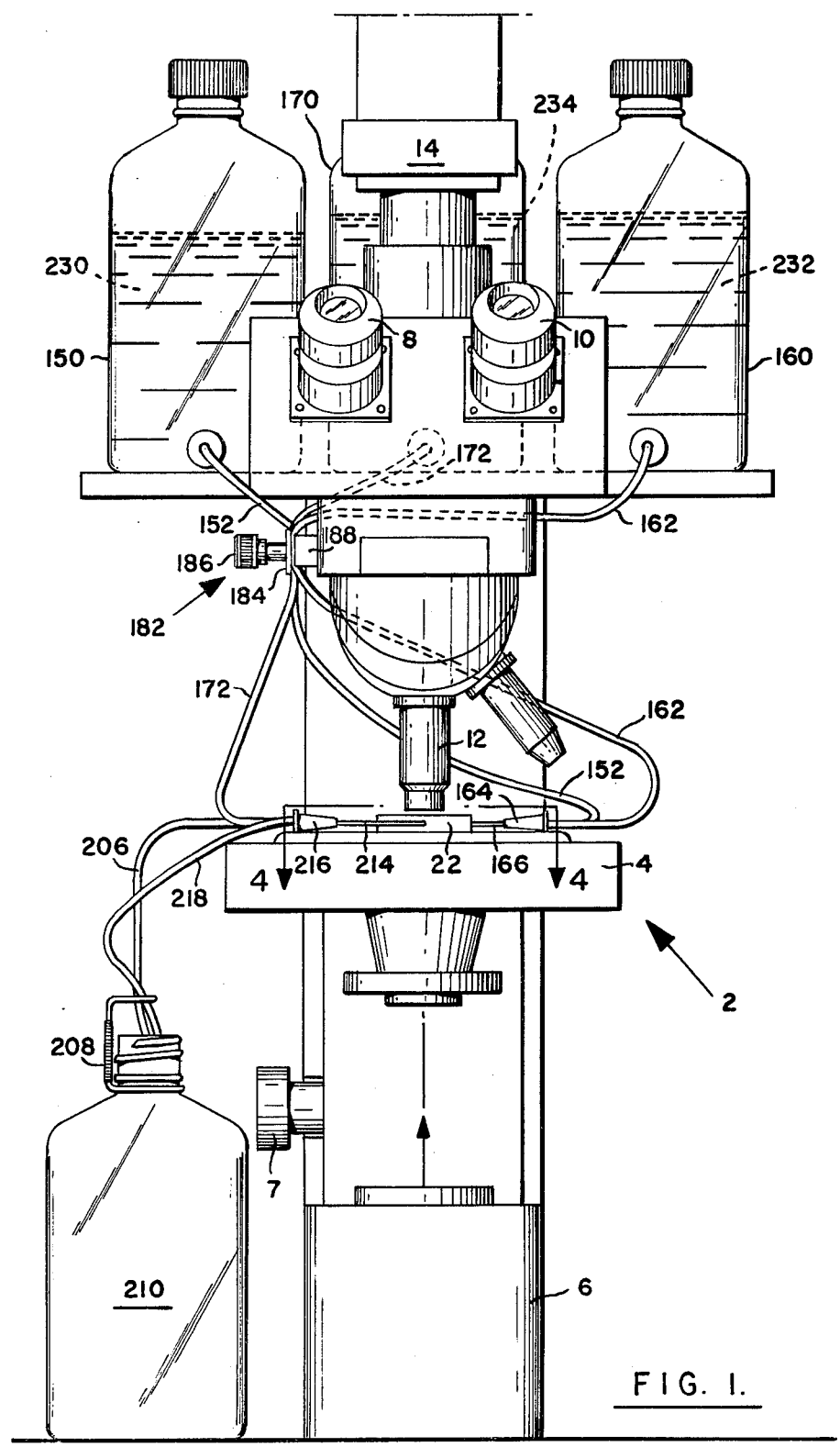
FIG. 1 is a front elevation partially broken away of a liquid flow viewing cell in accordance with the invention mounted on a microscope.

Referring to FIG. 1, a microscope 2 has a slide support 4 through which light is directed upwardly from a light source indicated at 6. The height of support 4 is adjusted by knob 7. Microscope 2 has eye pieces indicated at 8 and 10 and an objective lens system indicated at 12. A strobed vidicon indicated at 14 is mounted on microscope 2 for determination of the size of particles in a liquid being examined. All this apparatus is well known to the art and hence need not be detailed further here.

Adverting now to the invention, a liquid flow viewing cell 22 is shown mounted on slide support 4 in FIG. 1. Cell 22 is formed from a series of stacked plates (FIG. 3) including base plate 24, intermediate plates 26, 28, 30, 32, 34, 36, 38, 40 and 42 and top plate 44. Base plate 24 has secured thereto upstanding locating posts 50, 52, 54 and 56. Plates 26, 28, 30, 36, 42 and 44, each have an opening 58 in registry with post 50, an opening 60 in registry with post 52, an opening 62 in registry with post 54, and an opening 64 in registry with post 56. Plate 34 has openings 58 and 62 in registry with posts 50 and 54 while plate 32 has openings 60 and 64 in registry with posts 52 and 56, respectively. Plate 36 has openings 58 and 60 in registry with posts 50 and 52, respectively, and plate 38 has openings 62 and 64 in registry with posts 54 and 56, respectively.

Plate 24 has eight threaded openings 70 each for the reception of a machine screw 72. The portions of the other plates overlying one of the openings 70 in base plate 24 has a corresponding opening 74 in registry therewith to accommodate a screw 72. The upper ends of opening 74 in plate 44 are enlarged as indicated at 78 to recess the heads 80 of screw 72.

Base plate 24 has a central opening 82 for the passage of light and top plate 44 has a central viewing opening 84. Plate 28 has a side entering slot 88. Plates 32 and 34 have opposed central cutout portions 90 and 92, respectively, while plates 38 and 40 similarly have opposed central cutout portions 94 and 96, respectively. Plates 30 and 36 have central openings 100 and 102, respectively.

The above-discussed plates can be made from a wide variety of materials, for example metals such as brass, or a plastic such as an acrylic, for example methyl methylacrylate, a polyalkylene resin such as polyethylene or polypropylene, glass or quartz.

When base plate 24 and top plate 44 are made from a transparent material, the viewing openings 82 and 84 and plates 26 and 42 are unnecessary. It is required that plates 26 and 42 be formed of a transparent material, for example, glass or a plastic when plates 24 and 44 are opaque with viewing openings 82, 84.

Figure 3:
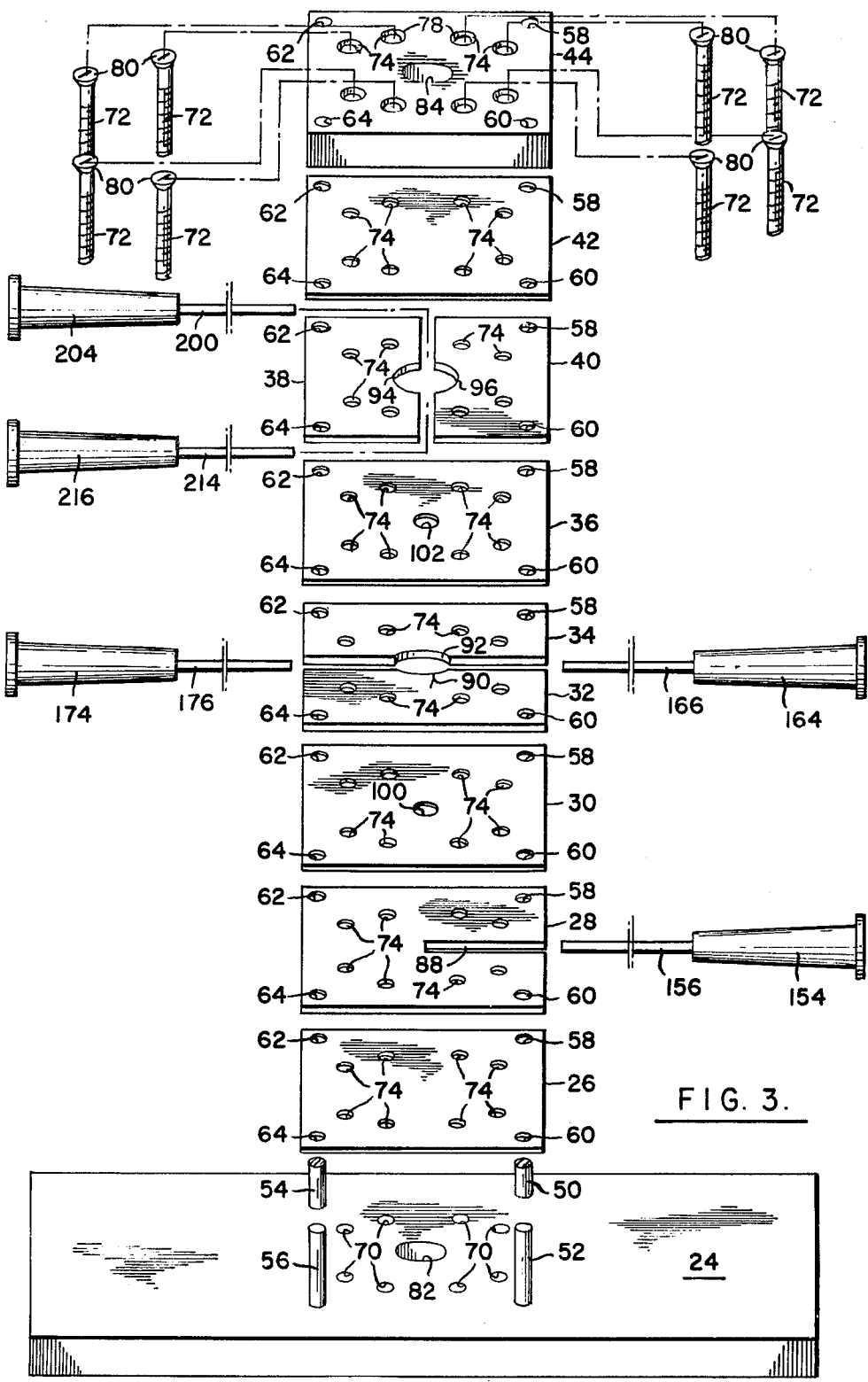
FIG. 3 is an exploded perspective view of elements of the viewing cell shown in FIG. 1.

The cell plates are assembled by stacking them in the order shown in FIG. 3 with pins 50, 52, 54 and 56, respectively, passing through openings 58, 60, 62 and 64 of the plates above base plate 24 to cause all of these plates to be accurately aligned so that the openings 74 are in registry with their respective openings 70 and so that the centers of openings 82, 100, 102 and 84 are aligned with each other and with the inner end of slot 88 and so that cutout portions 90, 92, 94 and 96 are properly aligned with openings 100 and 102 and with the plates 32 and 34 spaced the desired distance apart and the plates 38 and 40 spaced the desired distance apart. With the plates thus stacked, screws 72 are passed down through opening 74 and are threaded into opening 70 to tightly clamp all of the plates together.

Figure 4:
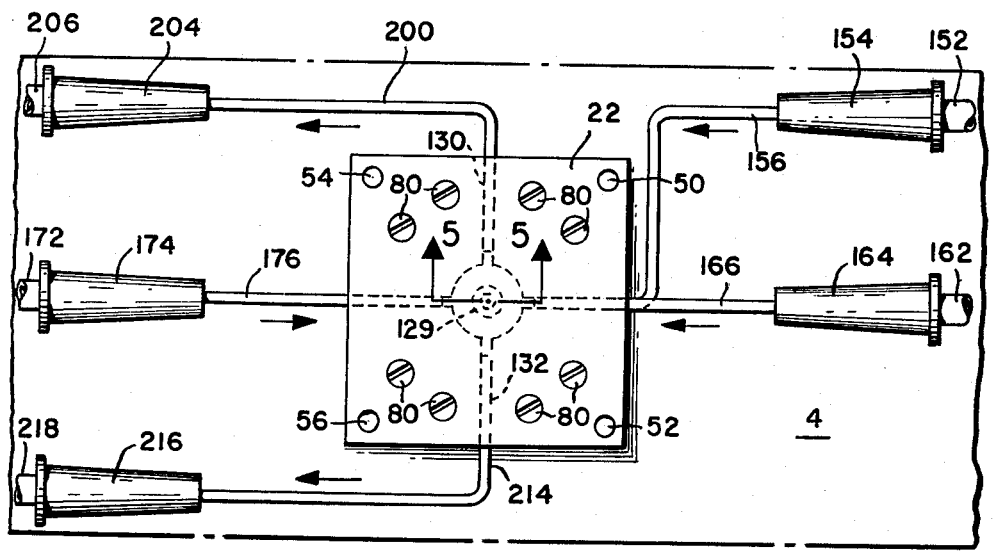
FIG. 4 is a view taken on the plane indicated by the line 4—4 in FIG. 1 and showing the top of the viewing cell.
Figure 5:
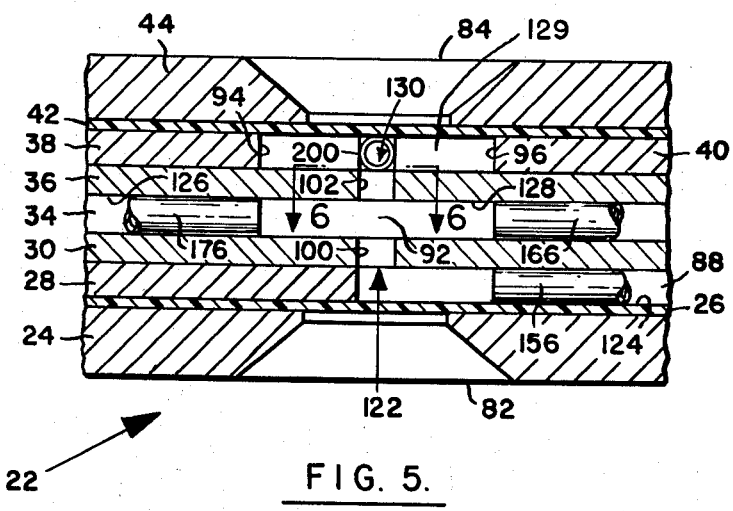
FIG. 5 is a vertical section, partially broken away, taken on the plane indicated by the line 5—5 in FIG. 4.

As best seen in FIG. 5, a main vertical passage 122 is formed by opening 100, cutout portion 92 of plate 34 and cutout portion 90 of plate 32 (not shown in FIG. 5), opening 102 in plate 36 and cutout portions 94 and 96 of plates 38 and 40, respectively. A supply passage 124 for supplying liquid to passage 122 is formed by virtue of slot 88 in plate 28 being clamped between plates 26 and 30. A pair of opposed supply passageways 126 and 128 for supplying liquid to the main passageway 122 are formed by spaced apart plates 34 and 32 (not shown in FIG. 5) and the adjoining plates 30 and 36. A discharge passageway 130 is formed by spaced apart plates 38 and 40 and the adjoining plates 36 and 42. Similarly, an exhaust passageway 132 as best seen in FIG. 4, is formed by spaced apart plates 38 and 40 and the adjoining plates 36 and 42.

Figure 2:
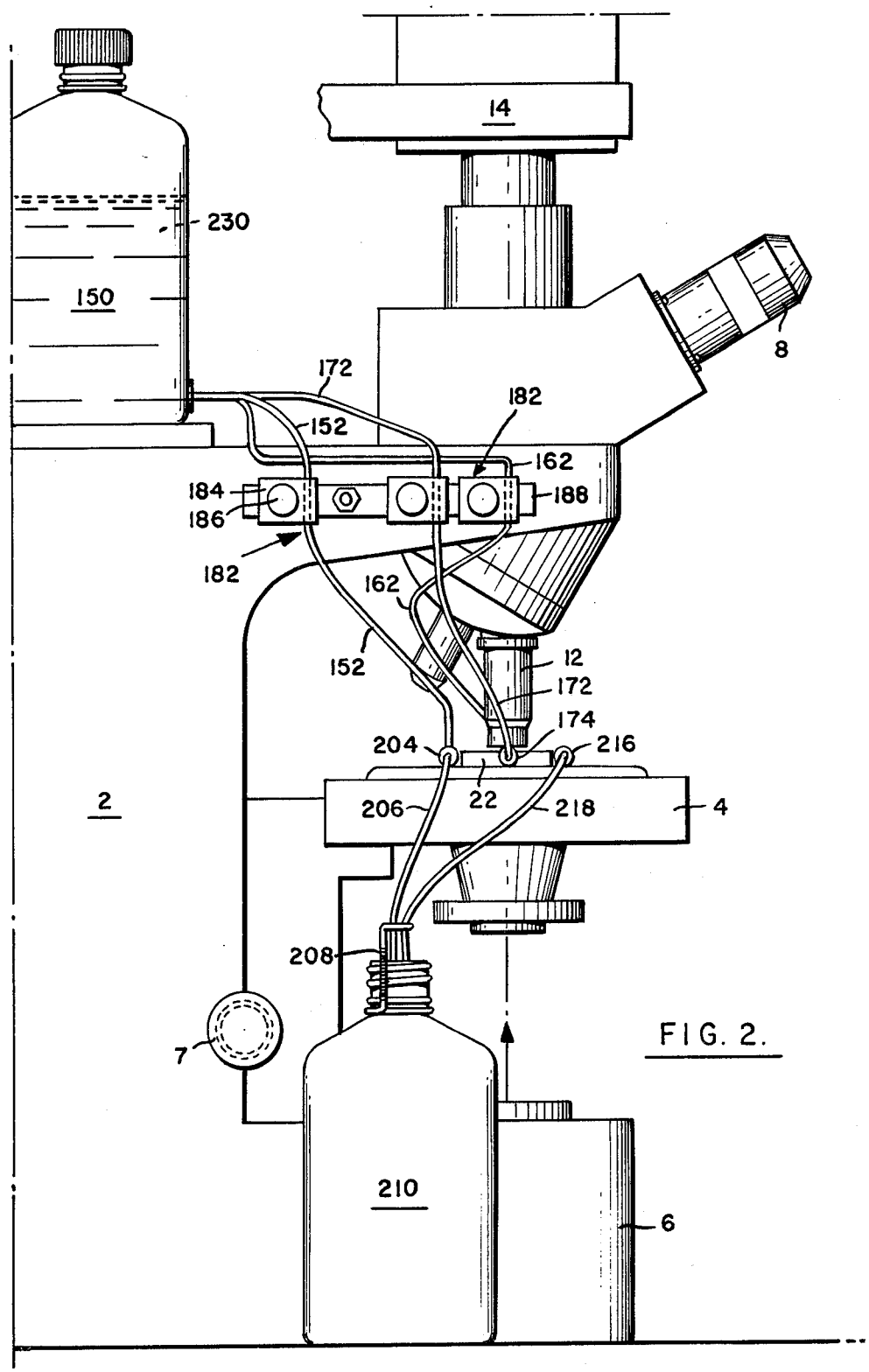
FIG. 2 is a side elevation of the apparatus shown in FIG. 1 partially broken away.

An elevated container 150 (FIG. 1) has its lower end connected to a flexible tube 152 which in turn is connected by a pressed fit to a female connecting member 154 (FIG. 4) secured to a tube 156 which is in turn secured by a pressed fit in passage 124 (FIG. 5) of cell 22. An elevated container 160 has its lower end connected to a flexible tube 162 which is connected by a pressed fit to a female connecting member 164 which is secured to a tube 166 connected by a pressed fit in passageway 128 (FIG. 5). An elevated container 170 has its lower end connected to a flexible tube 172 which in turn is connected to a female connecting member 174 which is secured to a tube 176 which in turn is secured by a pressed fit in passageway 126. Each of flexible tubes 152, 162 and 172 passes through a clamp 182 (FIGS. 1 and 2) having a clamping plate 184 through which passes a headed machine screw 186 which is threaded to a clamping bar 188 mounted on microscope 2.

A tube 200 is connected into passage 130 by a pressed fit and secured to a female fitting 204 which receives a flexible tube 206 by a pressed fit. Tube 206 passes through a guide 208 mounted on a waste bottle 210 into which tube 206 discharges. A tube 214 is connected into passage 132 by a pressed fit and in turn is secured to a female fitting 216 to which a flexible tube 218 is secured by a pressed fit. Tube 218 passes through guide 208 and discharges into waste bottle 210.

OPERATION

Figures 6, 7:
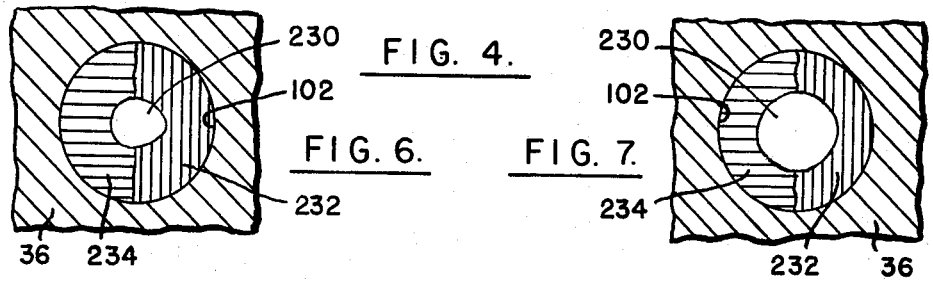
FIG. 6 is a section taken on the plane 6—6 in FIG. 5 showing the flow of liquid through the cell.
FIG. 7 is a section taken on the plane 6—6 in FIG. 5 showing the flow of liquid under different pressure conditions.

In operation, a test liquid 230 which for example is a clear liquid such as water containing particles of polystyrene is placed in bottle 150. A red liquid 232, for example, F D & C Red No. 2 in water is placed in bottle 160 and a blue liquid 234, for example, F D & C Blue No. 2 in water is placed in container 170. Lines 154, 164, 174, 200 and 214 are connected to cell 22. With light source 6 energized, cell 22 is centered on support 4. All the clamps 182 are in the closed position preventing flow into cell 22 through lines 152, 162 and 172. The clamp 182 controlling line 152 is opened permitting liquid 230 to flow through lines 152 and 156 into passage 124 and thence through passage 122 into chamber 129 and thence through passage 130 to tube 200 and tube 206 and through passage 132 to tubes 214 and 218 into waste bottle 210. With the light energized, platform 4 is adjusted to the proper height to maximize viewing liquid 230 as it discharges from passage 122 into chamber 129. The clamps 182 controlling lines 162 and 172 are now opened to cause the red liquid 232 to flow into tube 166 and passage 128 and thence into passage 122, and to cause the blue liquid 234 to flow into tube 176 and passage 126 and thence into passage 122. As best seen in FIG. 6, liquid 232 and liquid 234 together form a column of liquid surrounding liquid 230. By adjusting clamps 182 and hence the pressure of the liquids in passage 122, the diameter of the upwardly moving column of liquid 230 can be varied to make it the optimum size for the microscope 2. For example, by increasing the pressure in line 152 by opening up its associated clamp 182, or by reducing the pressure in lines 162 and 172, the diameter of the liquid 230 in passage 122 can be increased as shown in FIG. 7. The rate of flow is controlled in a like manner to control the time the particles remain in the viewing area of the microscope.

The color contrast provided by the particle free liquids 232 and 234 greatly facilitates viewing the liquid through the microscope eye pieces 8 and 10. Further, by way of illustration, the size of the particles in the test liquid can be determined by activating the strobe vidicon 14. Other associated equipment may be employed such as a photomultiplier for counting particles.

It will be appreciated that the flow through main passageway 122 can be reversed by introducing the test liquid into chamber 129 and discharging through passageway 88. Positive or negative pressure pumping can be used instead of gravity flow with the cell 22.

It will be understood that the above description is exemplary and is not intending to be limiting.

I claim:
 1. A liquid flow viewing cell comprising:
 a body having a substantially straight main passageway having opposed ends terminating within the body, a first liquid supply passageway connected adjacent to one end of the main passageway for supplying a column of liquid to be viewed in the main passageway, an exhaust passageway connected adjacent to the other end of the main passageway and a second liquid supply passageway connected to the main passageway at a point between the connections of the supply and exhaust passageways to the main passageway for supplying a column of liquid around the first column of liquid,
 said body being transparent opposite the ends of the main passageway, a system for moving liquid through each of the supply passageways and thence through the main passageway and the exhaust passageway, and a light substantially aligned with the main passageway and directed at the one end of the main passageway.

2. A viewing cell in accordance with claim 1 in which a third liquid supply passageway is connected to the said system and is connected to the main passageway at a point opposite the connection of the second supply passageway connected to the main passageway.

3. A viewing cell in accordance with claim 1 or claim 2 in which the liquid supplying system has valves for controlling the pressure of liquids in said liquid supply passageways.

4. A liquid flow viewing cell comprising:

a body having a substantially straight main passageway having opposed ends terminating within the body, a first liquid supply passageway connected adjacent to one end of the main passageway for supplying a column of liquid to be viewed in the main passageway, an exhaust passageway connected adjacent to the other end of the main passageway, second and third liquid supply passageways connected at opposite sides of said main passageway for supplying liquids to form a hollow column of liquid surrounding the first column of liquid, said body being transparent opposite the ends of the main passageway, a system for supplying liquids to each of the liquid supply passageways including a liquid supply line connected to each passageway and a valve in each liquid supply line for controlling the pressure of the liquid delivered to the cell, and a light aligned with the main passageway and directed at the end of the main passageway adjacent the first liquid supply passageway.

5. A method for presenting a stream of liquid for viewing comprising:

passing a first liquid to be viewed upwardly in a first column in a confined space to a transparent viewing panel lying transverse to the said column, p1 introducing a second liquid of a color differing from the color of the first liquid into the confined space to form a second upwardly moving hollow column exterior of the first column, carrying off the first and second liquids from the underside of the viewing panel, directing light at the lower end of the columns of liquid along the axis of the columns, and setting the pressures of the liquids in the columns to produce a desired circumference of the first column.

6. The method in accordance with claim 5 in which a third liquid of a color different from the first colored liquids is introduced into the confined space opposite the point of introduction of the second liquid.

* * * * *